United States Patent [19]

Zambias et al.

[11] Patent Number: 4,963,580
[45] Date of Patent: Oct. 16, 1990

[54] SUBSTITUTED 5-HYDROXY-2,3-DIHYDROBENZOTHIOPHENES AS INHIBITORS OF LEUKOTRIENE BIOSYNTHESIS

[75] Inventors: Robert A. Zambias, Springfield; Milton L. Hammond, Somerville, both of N.J.

[73] Assignee: Merck & Co., Inc., Rahway, N.J.

[21] Appl. No.: 442,497

[22] Filed: Nov. 27, 1989

Related U.S. Application Data

[63] Continuation of Ser. No. 259,372, Oct. 18, 1988, abandoned.

[51] Int. Cl.$^5$ .................... A61K 31/38; C07D 333/54
[52] U.S. Cl. ........................................ 514/443; 549/51
[58] Field of Search ........................... 549/51; 514/443

[56] References Cited

U.S. PATENT DOCUMENTS 4,621,091  11/1986  Tischler et al. ................. 514/337
4,663,344  5/1987   Durette et al. ................. 514/443

OTHER PUBLICATIONS

Chemical Abstracts, vol. 97, No. 3; Abst. No. 23566f to Clark et al. (1982).
Bordwell, F. G. and Stang, H., *Benzothiophene Chemistry, VII., Substitution Reactions of 5-Hydroxy and 5-Aminobenobenzothiophene Derivatives*, J. Amer. Chem. Soc., vol. 77, pp. 5939–5944, (Nov. 1955).
Feiser, L. F. and Kennelly, R. G., *A Comparison of Heterocyclic Systems with Benzene, IV, Thionaphthenequinones*, J. Amer. Chem. Soc., vol. 57, pp. 1611–1614, (Sep. 1935).
Fries, K.; Heering, H.; Hemmacke, K., and Siebert, G., *Untersuchungen in der Reihe des Thionaphtens*, Ann., vol. 527, pp. 83–113, (1936).
Oikawa, Y., and Yonemitsu, O., *A New Synthesis Method for Condensed Heterocycles, Carbazoles, Indoles, and Benzothiophenes, Based on Catalyzed Cyclization of Q-Keto Sulfoxides*, J. Org. Chem., vol. 41, pp. 1118–1124 (1976).
Kursanov, D. N.; Parnes, Z. N.; Loim, N. M., *Application of Ionic Hydrogenation to Organic Synthesis*, pp. 633–651, (Sep. 1974).

Primary Examiner—Joseph Paul Brust
Assistant Examiner—M. S. Howard
Attorney, Agent, or Firm—Curtis C. Panzer; Hesna J. Pfeiffer

[57] ABSTRACT

Position-4 and/or position-6 substituted 5-hydroxy-2,3-dihydrobenzothiophenes and analogs of the following general structural formula (I) are disclosed:

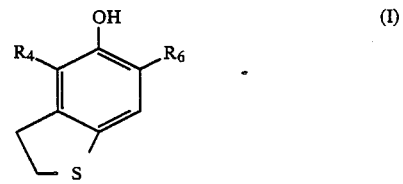

These compounds are found to be potent inhibitors of leukotriene biosynthesis.

7 Claims, No Drawings

SUBSTITUTED 5-HYDROXY-2,3-DIHYDROBENZOTHIOPHENES AS INHIBITORS OF LEUKOTRIENE BIOSYNTHESIS

This is a continuation of application Ser. No. 259,372, filed Oct. 18, 1988, now abandoned.

BACKGROUND OF THE INVENTION

The present invention relates to novel fourth and/or sixth position substituted 5-hydroxy2,3-dihydrobenzothiophenes useful as inhibitors of leukotriene biosynthesis.

Copending U.S. patent application Ser. No. 230,825 (CN 17729) of Caldwell et al filed Aug. 12, 1988, discloses and claims fourth and/or sixth position substituted 5-hydroxy-2,3 dihydrobenzofurans useful as inhibitors of leukotriene biosynthesis.

During the progression of inflammatory conditions, there is generally an appearance and/or presence of macrophages and lymphocytes, especially polymorphonuclear leukocytes. These cells are known to secrete various products in response to inflammatory stimuli. The arachidonic acid oxygenation products, in particular, have been identified as the critical mediators of various inflammatory conditions. Inhibition of arachidonic acid oxidation by enzyme inhibition has been explored as effective therapy. For example, non-steroidal anti-inflammatory drugs (NSAID) such as aspirin, indomethacin and diflunisal are known cyclooxygenase inhibitors which inhibit the process wherein arachidonic acid is oxygenated via cyclooxygenase to prostaglandins and thromboxanes.

Recently, it has been observed that certain leukotrienes are responsible for diseases related to immediate hypersensitivity reactions such as human asthma, allergic disorders, and skin diseases. In addition, certain leukotrienes and derivatives thereof are believed to play an important role in causing inflammation (B. Samuelsson, Science, 220, 568 (1983); D. Baily et al, Ann. Rpts. Med. Chem., 17, 203 (1982)).

Accordingly, pharmacological agents which are capable of inhibiting the formation or the release of a mediator and thereby interfere with the function of macrophages or polymorphonuclear leukocytes may also be effective agents in the treatment of various inflammatory conditions, e.g., pain, fever, rheumatoid arthritis, osteoarthritis, bronchial inflammation, inflammatory bowel disease, asthma, allergic disorders, skin diseases, cardiovascular disorder, glaucoma, emphysema, acute respiratory distress syndrome, spondylitis, lupus, gout and psoriasis.

The human polymorphonuclear leukocytes assay, has been found to be a useful indicator of the ability of compounds to inhibit leukotriene biosynthesis. Known inhibitors of leukotriene biosynthesis, agents such as phenidone and nordihydroguaiaretic acid, for example, are active in this assay (C. J. Blackwell and R. J. Flower, Prostaglandins, 16, 417 (1978); J. Chang, M.D. Skowronek, M. L. Cherney and A. J. Lewis, Inflammation, 8, 143 (1984)).

DETAILED DESCRIPTION OF THE INVENTION

This invention relates to novel compounds of formula (I)

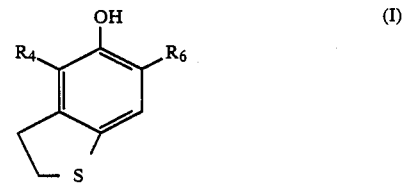

wherein: $R_4$ and $R_6$ are independently:
(a) hydrogen;
(b) $C_{2-6}$alkenyl;
(c) $C_{3-6}$alkyl;
(d) substituted $C_{3-6}$alkyl wherein the substituent is phenylthio, or pharmaceutically acceptable salts thereof.

In a preferred embodiment of the instant invention, the compounds of formula (I),
$R_4$ is hydrogen; and
$R_6$ is
(a) $C_{3-4}$alkenyl;
(b) $C_{3-4}$alkyl;
(c) phenylthio substituted $C_{3-4}$alkyl.

Specific species of the preferred embodiment are:
(a) 6-(propen-3-yl)-5-hydroxy 2,3-dihydrobenzothiophene;
(b) 6-propyl-2,3-dihydro-5-hydroxybenzothiophene;
(c) 6-t-butyl-2,3-dihydro-5-hydroxybenzothiophene; and
(d) 5-hydroxy-2,3-dihydro-6-(3-thiophenoxypropyl)-benzothiophene, or pharmaceutically acceptable salts thereof.

Less preferred species of the instant invention are:
(a) 5-hydroxy-2,3-dihydrobenzothiophene; and
(b) 4-(propen-3-yl)-5-hydroxy-2,3-dihydrobenzothiophene.

The compounds of the present invention are conveniently prepared using the procedures described generally below and more explicitly in the specific Examples thereafter.

The terms $R_4$ and $R_6$ are as defined in formula I and depict the point of substitution.

SCHEME I

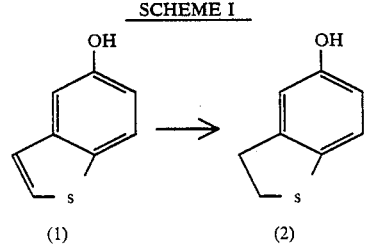

Scheme I depicts the preparation of the simplest member (2) of the invention, that is where $R_4$ and $R_6$ are both hydrogen. Triethylsilane is reacted with 5-hydroxybenzothiophene in a suitable solvent, e.g, trifluoroacetic acid (TFA) to yield the 5-hydroxy-2,3-dihydrobenzothiophene.

SCHEME II

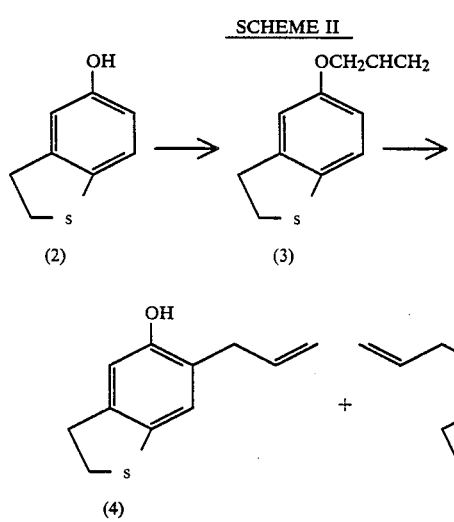

In reaction Scheme II, compound (2) is reacted with an alkenyl halide to form the corresponding 5-alkenyloxy-2,3-dihydrobenzothiophene (3). This in turn, by Claisen rearrangement, yields a mixture of the corresponding 4-alkenyl and 6alkenyl-5-hydroxy-2,3-dihydrobenzothiophenes.

SCHEME III

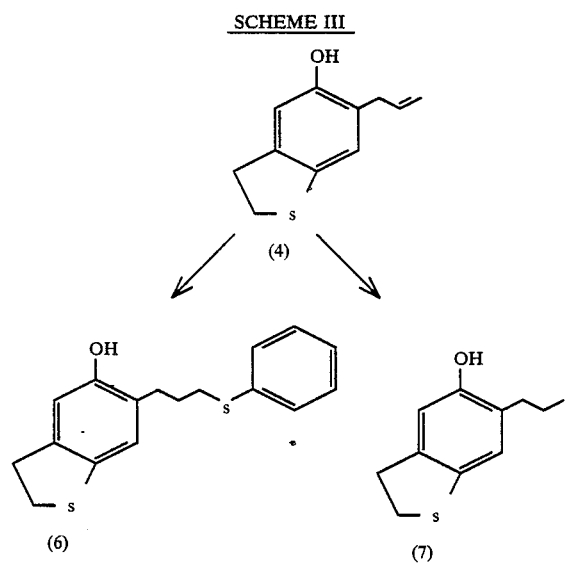

In reaction Scheme III, the 6-alkenyl-5hydroxy-2,3-dihydrobenzothiophene is reacted with thiophenol in the presence of a free radical initiator, e.g. azobisisobutyronitrile (AIBN) to yield the corresponding phenylthio substituted alkyl (6). Alternatively, the alkenyl can be reduced to the unsubstituted alkyl (7). While Scheme III shows reaction with the 6-alkenyl-5-hydroxy,2,3-dihydrobenzothiophene, the corresponding 4-alkenyl 5-hydroxy-2,3-dihydrobenzothiophene reacts in the same manner to yield the corresponding 4-alkenyl homolog.

SCHEME IV

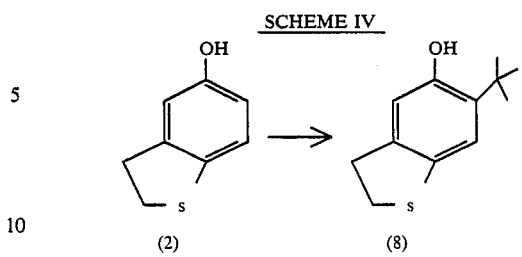

Alternatively, in reaction Scheme IV, the 5-hydroxybenzothiophene is reacted in suitable solvent with a tertiary alkanol using concentrated $H_2SO_4$ or another suitable acid catalyst to yield the 6-alkyl-5-hydroxy-2,3-dihydrobenzothiophene. While the t-butyl is shown, substitution of the appropriate tertiary alkanol could as easily have yielded other $C_{3-6}$ alkyls.

This invention also relates to a method of treating inflammation in patients in need of such treatment. Generally, an effective non toxic amount of a compound of formula (I) or a pharmaceutical composition thereof, particularly an especially preferred compound, is administered to the patient as the active constituent.

To demonstrate the utility of the present invention, representative novel compounds of formula I were evaluated for their ability to inhibit production of leukotriene $B_4$ ($LTB_4$) in isolated rat and human polymorphonuclear leukocytes (PMN). Other compounds known to inhibit leukotriene biosynthesis have been shown to have activity in this assay, and thus the assay is of value in predicting in vivo activity. The assay is conducted as follows:

A. Preparation of Human PMN. Human blood is obtained by antecubital venepuncture from consenting volunteers who denied having taken medication within the previous 7 days. The blood is immediately added to 10% (v/v) trisodium citrate (0.13 M) or 5% (v/v) sodium heparin (1000 IU/mL). PMNs are isolated from anticoagulated blood by dextran sedimentation and centrifugation through Ficoll Hypaque (specific gravity 1.077), essentially as described by Boyum. (Boyum, A., Scand. J. Clin. Lab. Invest. 1968, 21 (Supp 97), 77). Contaminating erthrocytes are removed by lysis following exposure to ammonium chloride (0.16 M) in Tris buffer (pH 7.65), and the PMNs resuspended at $5 \times 10^5$ cells/mL in HEPES (15 mM) buffered Hanks balanced salt solution containing $Ca^{2+}$ (1.4 mM) and $Mg^{2+}$ (0.7 mM), pH 7.4. Viability is assessed by Trypan blue exclusion and is typically greater than 98%.

B. Rat Peritoneal Polymorphonuclear leukocytes (PMN). Male Sprague Dawley rats were purchased from Taconic Farms, Germantown, NY. The animals were maintained on standard pellet diet and water ad lib. Elicited PMN were prepared from peritoneal exudates as follows: 8 ml of 12% sodium caseinate was injected intraperitoneally into male rats. After 18–20 hours, the rats were killed with $CO_2$ and the peritoneal cavities were lavaged with Eagle's MEM (pH 7.7) without $NaHCO_3$ but containing Earle's salts, L-glutamine, and 30 mM HEPES. The PMN were isolated by centrifugation, washed with MEM, filtered through lens paper to remove clumps, and adjusted to a concentration of $1 \times 10^7$ cells/ml.

C. Generation and Radiommumoassay of $LTB_4$. PMNs (0.5 mL; $2.5 \times 10^5$ cells) are placed in plastic tubes and incubated (37° C., 2 min) with test compounds at the desired concentration or vehicle control (DMSO, final concentration 0.2%). The synthesis of LTB$_4$ is initiated by the addition of calcium inophore A23187 (final concentration 10 μM) or vehicle on control samples and allowed to proceed for 5 minutes at 37° C. The reactions are then terminated by the addition of cold methanol (0.25 mL) and samples of the entire PMN reaction mixture are removed for radiommunoassay of LTB$_4$.

Samples (50 μl) of authentic LTB$_4$ of known concentration in radiommunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes.

Thereafter [3H]-LTB$_4$ (10 nCu in 100 μl RIA buffer) and LTB$_4$ antiserum (100 μL of a 1:3000 dilution in RIA buffer) are added and the tubes vortexed. Reactants are allowed to equilibrate by incubation overnight at 4° C. To separate antibody-bound from free LTB$_4$, aliquots (50 μL) of activated charcoal (3% activated charcoal in RIA buffer containing 0.25% Dextran T-70) were added, the tubes vortexed, and allowed to stand at room temperature for 10 minutes prior to centrifugation (1500×g; 10 min; 4° C). The supernatents containing antibody-bound LTB$_4$ are decanted into vials and Aquasol 2 (4 mL) was added. Radioactivity is quantified by liquid scintillation spectrometry. Preliminary studies established that the amount of methanol carried into the radioimminoassay did not influence the results. The specificity of the antiserium and the sensitivity of the procedure have been described in detail elsewhere. (Rokach, J.; Hayes, E. C.; Griard, Y.; Lombardo. D. L.; Maycock, A. L.; Rosenthal, A. S.; Young, R. N.; Zamboni, R.; Zweerink, H. J. Prostaglandins Leukotrienes and Medicine 1984, 13, 21). The amount of LTB4 produced in test and control approx. 20ng/10$^6$ cells) samples are then calculated. Inhibitory dose response curves are constructed using a four parameter algorithm and from these the IC$_{50}$ values are determined.

Standard compounds phenidone and nordihydroguaiacetic acid, when evaluated by the above described in vitro test, demostrate IC$_{50}$ values for LTB$_4$ inhibition of 9250 nM and 86 nM respectively. As also indicted below representative compounds within the scope of the present invention have been found to possess in vitro activities superior to those of these standard compounds.

| | Polymorphonuclear Leucocyte (PMN) Activity of Specific Compounds | | |
|---|---|---|---|
| R$_4$ | R$_6$ | Rat PMN IC$_{50}$ (nM) | Human PMN IC$_{50}$ (nM) |
| H | H | 5230 | |
| H | —CH$_2$CH=CH$_2$ | 190 | 319 |
| H | —C$_3$H$_8$ | 211 | 326 |
| H | —C$_4$H$_{10}$ | 207 | 142 |
| —CH$_2$CH=CH$_2$ | H | 887 | 2259 |

For the treatment of inflammation, arthritis conditions, psoriasis, asthma, or other diseases mediated by prostaglandins, a compound of formula (I) may be administered orally, topically, parenterally, by inhalation spray or rectally in dosage unit formulations containing conventional non toxic pharmaceutically acceptable carriers, adjuvants and vehicles. The term parenteral as used herein includes subcutaneous injections, intravenous, intramuscluar, intravascular injection or infusion techniques. In addition to the treatment of warm blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lonzenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and pre serving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelation or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut (arachis) oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxy propylmethylcellulose, sodium alginate, polyvinyl pyrrolidone, gum tragacanth and gum acacia; dispersing or wetting agents may be a naturally occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial ester derived from fatty acids and hexitol anhydrides, for example, polyoxyethylene sorbitan monooleate. The said aqueous suspensions may also contain one or more preservatives, for example, ethyl, or n propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules are suitable for the preparation of an aqueous suspension by mixing them with water. They provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil in water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally occurring phosphatides, for example, soy bean, lecithin, and esters or partial ester derived from fatty acids and hexitol anhydrides, for example, sorbitan mono oleate, and condensation products of the said partial esters with enthylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sebacate, ethyl caproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.2 mg to 140 mg per kilogram of body weight per day are useful in the treatment of the above-indicated condition (10 mg to 7 gms per patient per day). For example, inflammation is effectively treated by the administration from about 0.5 to 50 mg of the compound per kilogram of body weight per day (25 mg to 5 gms per patient per day).

The amount of active ingredient that may be combined with the carrier materials to produce a single dosage will vary depending upon the host treated and the particular mode of administration. Dosage unit forms will generally contain from about 25 mg to about 1 g of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate the preparation of the compounds of the formula (I) and as such are not to be considered as limiting the invention set forth in the claims appended hereto.

EXAMPLE 1

Preparation of 5-Hydroxy-2,3-dihydrobenzothiophene

To a warm mixture of 5-hydroxy benzothiophene (10.0 g, 66.58 mmole) (Fieser & Kennelly, J. Amer. Chem. Soc., Vol. 57, pp 1611–1614, (1935)) in 100 mL TFA was added triethylsilane (19.35 g, 166.45 mmole, 2.5 eq.) The resulting purple solution was heated to 55° C. under $N_2$ overnight. After 24 hours a sample removed for NMR analysis showed the reaction to be about 80% complete. Much of the original purple color had also been discharged at this point. An additional portion of triethylsilane (3.9 g, 0.5 eq) was added and the heating was continued for another 24 hours. NMR analysis at the 48 hour time point showed virtually no change from the 24 hour time point. Most of the TFA was distilled off under reduced pressure (40 mmHg). The residue was taken up in 300 mL $H_2O$ and rendered alkaline (pH=10 to pH paper) with 5N NaOH and washed with ether (2×100 mL). The aqueous phase was acidified with 2N HCl and extracted with ether (3×200 mL). The combined organic extracts were washed with sodium bicarbonate (1×100 mL), $H_2O$ (1×100 mL) and brine (1×100 mL). Drying over $Na_2SO_4$ and concentration gave 4.7 g (46.5%) gray solids. Purification by preparative chromatography on a Waters 500A prep HPLC using 2 columns and 90/10 vol/vol hexane/EtOAc to elute afforded 3.0 g (30%) pure material (single spot by TLC analysis) mp 87°–89° C.

| Analysis: | C; | H; | S; |
| --- | --- | --- | --- |
| Calcd: | 63.14 | 5.30 | 21.07 |
| Found: | 63.23 | 5.30 | 20.97 |

EXAMPLE 2

Preparation of 5-Allyloxy-2,3-dihydrobenzothiophene

To a solution of 5-hydroxy-2,3-dihydrobenzothiophene (1.53 g, 10.05 mmoles) in 200 mL acetone was added $K_2CO_3$ (12.5 g, 90.45 mmoles) with good mechanical stirring. The suspension was warmed and allyl bromide (4.86 g, 40.20 mmoles) was added in one portion. The reaction mixture was then heated to reflux overnight. After cooling, the solids were removed by filtration and the filtrate concentrated. The residue was taken up in 50/50 vol/vol hexane/methylene chloride and refiltered to remove the remaining salts. Concentration afforded 3.2 q crude product (a yellow oil) which was purified by flash chromatography (3% EtOAc in hexane to elute) to give 1.61 g pure product (83.4%) as an oil.

| Analysis: | C; | H; | S; |
| --- | --- | --- | --- |
| Calcd: | 68.73 | 6.29 | 16.68 |
| Found: | 68.71 | 6.33 | 16.44 |

EXAMPLE 3

Preparation of 6-Allyl-5-hydroxy-2,3-dihydrobenzothiophene

To a solution of $BCl_3$ in methylene chloride (5.5 mL, 1.0M, 5.5 mmole) under $N_2$ at −25° C. was added dropwise a solution of 5-allyloxy-2,3-dihydrobenzothiophene (1.0 g, 5.2 mmole) in methylene chloride (10 mL) keeping the temperature between −25° and −15° C. (10 minutes). The reaction mixture was stirred at −15° C. for 15 minutes. The cooling bath was then removed and the reaction mixture allowed to stir for another 1.5 hours. The reaction mixture was then poured into ice water (70 mL). An additional portion of methylene chloride (10 mL) was added and the layers separated. The aqueous layer was extracted an additional 2×20 mL methylene chloride and the combined organic layers were washed with NaHCO$_3$ (sodium bicarbonate) (1×20 mL), H$_2$O (1×20 mL) and brine (1×20 mL). After drying over Na$_2$SO$_4$, filtration and concentration afforded 0.56 g crude product. Purification by flash chromatography (90/10 hexane/EtOAc to elute) afforded, in order of elution: 64 mg (6.4%) 4-allyl-2,3-dihydrobenzothiophene (oil) 204 mg (20.4% 6-allyl-2,3-dihydrobenzothiophene (oil) and 146 mg (18.4%) 5-hydroxy-2,3-dihydrobenzothiophene.

| Analysis: | C; | H; | S; |
|---|---|---|---|
| Calcd: | 68.73 | 6.29 | 16.68 |
| Found: | 67.91 | 6.30 | 16.39 |

EXAMPLE 4

Preparation of 6-propyl-2,3-Dihydrobenzothiophene

A solution of 6-allyl-2,3-dihydrobenzothiophene (95 mg, 0.49 mmole) in 10 mL absolute ethanol was hydrogenated at 40 psi over 20 mg 10% Pd/C at room temperature overnight. TLC (90/10, hexane/EtOAc) indicated the reaction to be complete. The catalyst was filtered off through a celite pad and the filtrate concentrated down to afford 96 mg crude product as an oil. Purification by flash chromatography (90/10, hexane/EtOAc) afforded 75 mg white solids mp 58°-60° C. (78%).

| Analysis: | C; | H; | S; |
|---|---|---|---|
| Calcd: | 68.00 | 7.26 | 16.20 |
| Found: | 67.91 | 7.13 | 16.45 |

EXAMPLE 5

Preparation of 6-t-Butyl-2,3-dihydrobenzothiophene

To a solution of 5-hydroxy-2,3-dihydrobenzothiophene (500 mg, 3.28 mmoles) in 20 mL benzene in a sealable tube was added t-butanol (729 mg, 9.84 mmoles, 3.0 eq) and 0.4 mL concentrated H$_2$SO$_4$. The tube was sealed and the reaction mixture heated at 60° C. for 24 hours. The reaction mixture was cooled, diluted with water (50 mL) and extracted 2×25 mL ether. The combined extracts were washed with sodium bicarbonate (1×25 mL), H$_2$O (1×25 mL) and brine (1×25 mL). The organic layer was then dried over Na$_2$SO$_4$, filtered and concentrated to give 220 mg crude product. Purification by flash chromatography (90/10, hexane/EtOAc) afforded 125 mg pure product (18%) mp 90°-93° C.

| Analysis: | C; | H; | S; |
|---|---|---|---|
| Calcd: | 69.19 | 7.74 | 15.39 |
| Found: | 69.0 | 7.57 | 15.72 |

EXAMPLE 6

Preparation of 5-Hydroxy-2,3-dihydro-6-(3-thiophenoxypropyl)-benzothiophene

To a solution of 5-hydroxy-6-allyl-2,3-dihydrobenzothiophene (125 mg, 0.65 mmole) in 0.5 mL thiophenol was added 28 mg AIBN. The reaction mixture was purged with nitrogen and heated to 90° C. for 3 hours. TLC analysis (90/10 hexane/EtOAc) showed the reaction to be complete. The reaction mixture was diluted with 25 mL saturated sodium bicarbonate and extracted 3×25 mL EtOAc. The combined organics were washed with sodium bicarbonate (2×25 mL), H$_2$O (1×25 mL) and brine (1×25 mL). Drying over Na$_2$SO$_4$, filtration and concentration afforded 568 mg crude product as an oil. Purification by flash chromatography (90/10, hexane/EtOAc) 126 mg (64%) pure product NMR 287 MS181.

| Analysis: | C; | H; | S; |
|---|---|---|---|
| Calcd: | 67.51 | 6.00 | 21.20 |
| Found: | 67.68 | 6.17 | 21.19 |

While presently preferred embodiments of the invention have been described in detail for purposes of disclosure, numerous alternatives will readily suggest themselves to those skilled in the art and are encompassed within the principles of the invention and the scope of the appended claims.

What is claimed is:

1. A compound of formula (I)

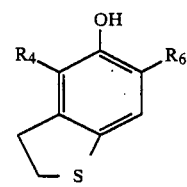

wherein: R$_4$ and R$_6$ are independently selected from:
 (a) hydrogen;
 (b) C$_{2-6}$alkenyl;
 (c) C$_{3-6}$alkyl; and
 (d) substituted C$_{3-6}$alkyl wherein the substitutent is phenylthio or pharmaceutically acceptable salts thereof.

2. A compound according to claim 1 wherein R$_4$ is hydrogen.

3. A compound according to claim 2 wherein: R$_6$ is
 (a) C$_{3-4}$alkenyl;
 (b) C$_{3-4}$alkyl;
 (c) phenylthio substituted C$_{3-4}$ alkyl.

4. A compound according the claim 3 selected from the group consisting of:
 (a) 6-(propen-3-yl)-5-hydroxy-2,3-dihydrobenzothiophene;
 (b) 6-propyl-2,3-dihydro-5-hydroxybenzothiophene;
 (c) 6-t-butyl-2,3-dihydro- 5-hydroxybenzothiophene; and (d) 5-hydroxy-2,3-dihydro-6-(3 thiophenoxypropyl)-benzothiophene, or pharmaceutically acceptable salts thereof.

5. A pharmaceutical composition for treating leukotriene mediated diseases comprising a pharmaceutical carrier and a non-toxic effective amount of a compound, according to claim 1.

6. A pharmaceutical composition according to claim 5 wherein the compound is selected from the group consisting of:

(a) 6-(propen-3-yl)-5-hydroxy-2,3-dihydrobenzothiophene;
(b) 6-propyl-2,3-dihydro-5-hydroxybenzothiophene;
(c) 6-t-butyl-2,3-dihydro-5-hydroxybenzothiophene; and
(d) 5-hydroxy-2,3-dihydro-6-(3-thiophenoxypropyl)-benzothiophene, or pharmaceutically acceptable salts thereof.

7. A method of treating leukotriene mediated diseases comprising the administration to a subject in need of such treatment a therapeutically effective amount of a compound according to claim 1.

* * * * *